US00PP21370P2

(12) United States Plant Patent
Kaagman

(10) Patent No.: US PP21,370 P2
(45) Date of Patent: Oct. 5, 2010

(54) ***DAHLIA* PLANT NAMED 'GOLIA ROSBI'**
(50) Latin Name: ***Dahlia* hybrid**
Varietal Denomination: Golia Rosbi

(75) Inventor: Pim Kaagman, Andijk (NL)

(73) Assignee: Goldsmith Seeds Europe B.V., Andijk (NL)

( * ) Notice: Subject to any disclaimer, the term of this patent is extended or adjusted under 35 U.S.C. 154(b) by 0 days.

(21) Appl. No.: 12/584,549

(22) Filed: Sep. 8, 2009

(51) Int. Cl.
*A01H 5/00* (2006.01)

(52) U.S. Cl. ..... Plt./321
(58) Field of Classification Search ..... Plt./321
See application file for complete search history.

*Primary Examiner*—Susan B McCormick Ewoldt
(74) *Attorney, Agent, or Firm*—S. Matthew Edwards

(57) ABSTRACT

A new *Dahlia* plant named 'Golia Rosbi,' particularly distinguished by the large red-purple and white bi-colored 'collerette' type flowers, full and compact plant habit with excellent branching, medium dark green foliage, and good floriferiousness.

1 Drawing Sheet

Latin name of the genus and species of the plant claimed: *Dahlia* hybrid.

Varietal denomination: 'Golia Rosbi'.

BACKGROUND OF THE NEW PLANT

The present invention comprises a new *Dahlia*, botanically known as *Dahlia* hybrid and hereinafter referred to by the variety name 'Golia Rosbi.'

'Golia Rosbi' is a product of a planned breeding program. The new cultivar 'Golia Rosbi' has large red-purple and white bi-colored 'collerette' type flowers, full and compact plant habit with excellent branching, medium dark green foliage, and good floriferiousness.

'Golia Rosbi' originates from a sibling cross hybridization in a controlled breeding program in Andijk, Netherlands. The pollination took place in August 2006 and the seed sown in November 2006. 'Golia Rosbi' was selected as one flowering plant within the progeny of the stated cross in February 2007 in a controlled environment in Andijk, Netherlands.

The female parent was an unpatented, proprietary hybrid seedling identified as 'D05-100-2,' a scarlet and yellow colored flower. 'D05-100-2' has more ray florets, a more open plant habit and a little larger in size than 'Golia Rosbi.'

The male parent of 'Golia Rosbi' was an unpatented, proprietary hybrid seedling identified as 'D05-100-4,' a scarlet and yellow. 'D05-100-4' has more ray florets, a more open plant habit, and is a little larger in size with less vigor than 'Golia Rosbi.'

The first act of asexual reproduction of 'Golia Rosbi' was accomplished when vegetative cuttings were propagated from the initial selection in February 2007 in a controlled environment in Andijk, Netherlands.

Horticultural examination of plants grown from cuttings of the plant initiated in February 2007 in Andijk, Netherlands, and continuing thereafter, has demonstrated that the combination of characteristics as herein disclosed for 'Golia Rosbi' are firmly fixed and are retained through successive generations of asexual reproduction.

'Golia Rosbi' has not been observed under all possible environmental conditions. The phenotype may vary significantly with variations in environment such as temperature, light intensity and day length.

A Plant Breeder's Right for this cultivar was applied for in Canada in January 2009. 'Golia Rosbi' has not been made publicly available more than one year prior to the filing of this application.

BRIEF DESCRIPTION OF THE PHOTOGRAPHS

The accompanying photographic drawings show typical flower and foliage characteristics of 'Golia Rosbi' with colors being as true as possible with an illustration of this type. The photographic drawing shows in FIG. 1, a flowering potted plant of the new variety and in FIG. 2, a close-up of the flowers.

DETAILED BOTANICAL DESCRIPTION

The plant descriptions and measurements were taken in Hillscheid, Germany, in May 2009 on plants that were growing in 12 cm pots on benches in a greenhouse trial, and were about 14 weeks old. The aforementioned whole plant photograph was taken in early June 2009 on plants that were about 16 weeks old. The flower close-up photograph was taken in April 2009 on plants that were about 14 weeks old. Both photographs were taken in Hillscheid, Germany.

Color references are made to The Royal Horticultural Society Colour Chart (R.H.S.) 2001.

BRIEF SUMMARY OF INVENTION

The following traits have been repeatedly observed and are determined to be basic characteristics of the new variety. The combination of these characteristics distinguishes this *Dahlia* as a new and distinct variety.

TABLE 1

DIFFERENCES BETWEEN THE NEW VARIETY 'GOLIA ROSBI' AND A SIMILAR VARIETY

| | 'Golia Rosbi' | 'Balnovburs' (U.S. Plant Pat. No. 15,326) |
|---|---|---|
| General flower color | Red-purple bi-colored | Greyed-red bi-colored |
| Leaf size | Wider | Narrower |
| Plant height | Shorter | Taller |

TABLE 1-continued

DIFFERENCES BETWEEN THE NEW VARIETY 'GOLIA ROSBI' AND A SIMILAR VARIETY

| | 'Golia Rosbi' | 'Balnovburs' (U.S. Plant Pat. No. 15,326) |
|---|---|---|
| Stem color | Medium green | More yellow-green |
| Foliage shape | Elliptical to rhomboidal | Ovate |

Plant:
- *Form, growth and habit.*—Compact and mounding, good branching.
- *Plant height.*—13-14 cm.
- *Plant height (inflorescence included).*—15-17 cm.
- *Plant width.*—16-18 cm.
- *Garden performance and tolerance to weather.*—Good.
- *Crop time to flowering.*—About 9-12 weeks.

Roots:
- *Number of days to initiate and develop roots.*—About 21-28 days at about 21 degrees C.
- *Type.*—Fine, fibrous, free branching.
- *Color.*—RHS N155B but whiter.

Foliage:
- *Arrangement.*—Opposite, single, simple.
- *Immature, leaf color, upper surface.*—RHS 143A.
- *Lower surface.*—RHS 138C but slightly more greyish.
- *Mature, leaf color, upper surface.*—RHS 137A to RHS 137B.
- *Lower surface.*—RHS 139D.
- *Length.*—Up to 7.0 cm.
- *Width.*—Up to 5.5 cm.
- *Shape.*—Elliptical to rhomboidal.
- *Base shape.*—Shortly attenuate.
- *Apex shape.*—Obtuse.
- *Margin.*—Crenate with short spines.
- *Texture, upper surface.*—Nearly glabrous, hirsute along the vein.
- *Lower surface.*—Glabrous.
- *Venation color, upper.*—Indistinct from leaf surface color.
- *Venation color, lower.*—RHS 144B.
- *Petioles color.*—RHS 137D to RHS 143A.
- *Petioles length.*—About 0.7-1.3 cm.
- *Diameter of petiole.*—0.3-0.4 cm at the midsection.
- *Texture.*—Smooth, glabrous.

Stem:
- *Average quantity of main branches per plant.*—About 25-30.
- *Color of stem.*—RHS 143C.
- *Length of stem.*—6-9 cm.
- *Diameter.*—0.3-0.4 cm at the midsection.
- *Length of internodes.*—1-3 cm.
- *Texture.*—Smooth, glabrous.
- *Color of peduncle.*—RHS 143B to 143C.
- *Length of peduncle.*—3-5 cm.
- *Peduncle diameter.*—0.2 cm.
- *Texture.*—Smooth, glabrous.

Inflorescence:
- *Type.*—Inflorescences borne on terminals relatively close above foliage, upward and outward directed.
- *Blooming habit.*—Continuous throughout the growing season.
- *Average quantity of inflorescences per plant.*—20-25.
- *Average quantity of inflorescences per lateral stem.*—2-3.
- *Lastingness of individual blooms on the plant.*—7-12 days.
- *Fragrance.*—None.

Bud (just before opening):
- *Color.*—RHS 70C.
- *Length.*—1.7 cm.
- *Width.*—1.3-1.4 cm.
- *Shape.*—Initially round, turning ovate and cylindrical with lengthening of the rays.

Immature inflorescence:
- *Diameter.*—About 4.5-6.0 cm.
- *Color of ray florets, upper surface.*—Mainly RHS 61A to RHS 61B with RHS N155B but whiter basally.
- *Lower surface.*—RHS70A to RHS70B, sometimes as pale as RHS69B.

Mature inflorescence:
- *Diameter.*—6.3-6.5 cm.
- *Depth.*—1.3 cm.
- *Total diameter of 'disc'.*—1.3-1.4 cm.
- *Recepticle height.*—0.5-0.6 cm.
- *Recepticle diameter.*—0.9-1.0 cm.

Ray florets:
- *Average quantity of florets.*—8-10.
- *Color of florets, upper surface.*—RHS N66A with RHS N155B but whiter basally; fading to RHS N66B to RHS 67B. Sometimes the white basal blotch runs upwards towards the apex forming several stripes.
- *Lower surface.*—RHS 71D centrally, RHS 73A at the margins and RHS 155A to RHS 157A stripes.
- *Length.*—2.5-2.8 cm.
- *Width.*—1.6-1.7 cm.
- *Shape.*—Broadly elliptical.
- *Base shape.*—Fused.
- *Apex shape.*—Obtuse.
- *Margin.*—Entire.
- *Texture, upper surface.*—Papillose; glabrous.
- *Lower surface.*—Papillose; glabrous.
- *Number of petaloids.*—Rarely 1 per ray floret.
- *Color of petaloids, upper surface.*—RHS N66A with RHS N155B but whiter basally; fading to RHS N66B to RHS 67B.
- *Lower surface.*—RHS 71D centrally, RHS 73A at the margins.
- *Length.*—About 1.0-1.2 cm.
- *Width.*—About 0.6-0.7 cm.
- *Shape.*—Lanceolate to narrowly elliptical.
- *Apex shape.*—Acute to obtuse.

Disc florets:
- *Average quantity of florets.*—About 25-30.
- *Color of florets.*—RHS 5B.
- *Length.*—1.3 cm.
- *Width.*—0.2 cm at opening.
- *Shape.*—Tube-shaped.
- *Apex shape.*—Acute, 5-pointed.

Phyllaries:
- *Average quantity.*—About 8-9.
- *Color, upper surface.*—RHS N144A; but appears almost semi-transparent.
- *Lower surface.*—RHS N144A; but appears almost semi-transparent.
- *Length.*—1.0-1.5 cm.
- *Width.*—0.5-0.6 cm.
- *Shape.*—Ligulate.

*Base shape.*—Fused.
*Apex shape.*—Rounded to obtuse.
*Margin shape.*—Entire.
*Texture, upper surface.*—Smooth; glabrous.
*Lower surface.*—Smooth; glabrous.

Reproductive organs:

*Gyneocium.*—Present on disc florets only.
*Pisil quantity.*—1 per floret.
*Length.*—1.2 cm.
*Style color.*—RHS 145C.
*Style length.*—0.8 -0.9 cm.
*Stigma color.*—RHS 13A.
*Stigma shape.*—Bi-furchate (bi-lobed).
*Ovary color.*—RHS 144C.
*Andreocium.*—Present on disc florets only.
*Stamens quantity.*—5 united.
*Color of filaments.*—RHS 155A.
*Length filaments.*—0.4-0.5 cm.
*Anther color.*—RHS 12A.
*Anther length.*—0.5-0.6 cm.
*Color of pollen.*—RHS 13A.
*Pollen amount.*—Abundant.
*Fertility/seed set.*—Not observed on this hybrid.

Disease/pest resistance: Disease resistance or susceptibility has not been observed on this hybrid.

What is claimed is:

1. A new and distinct variety of *Dahlia* plant named 'Golia Rosbi,' substantially as illustrated and described herein.

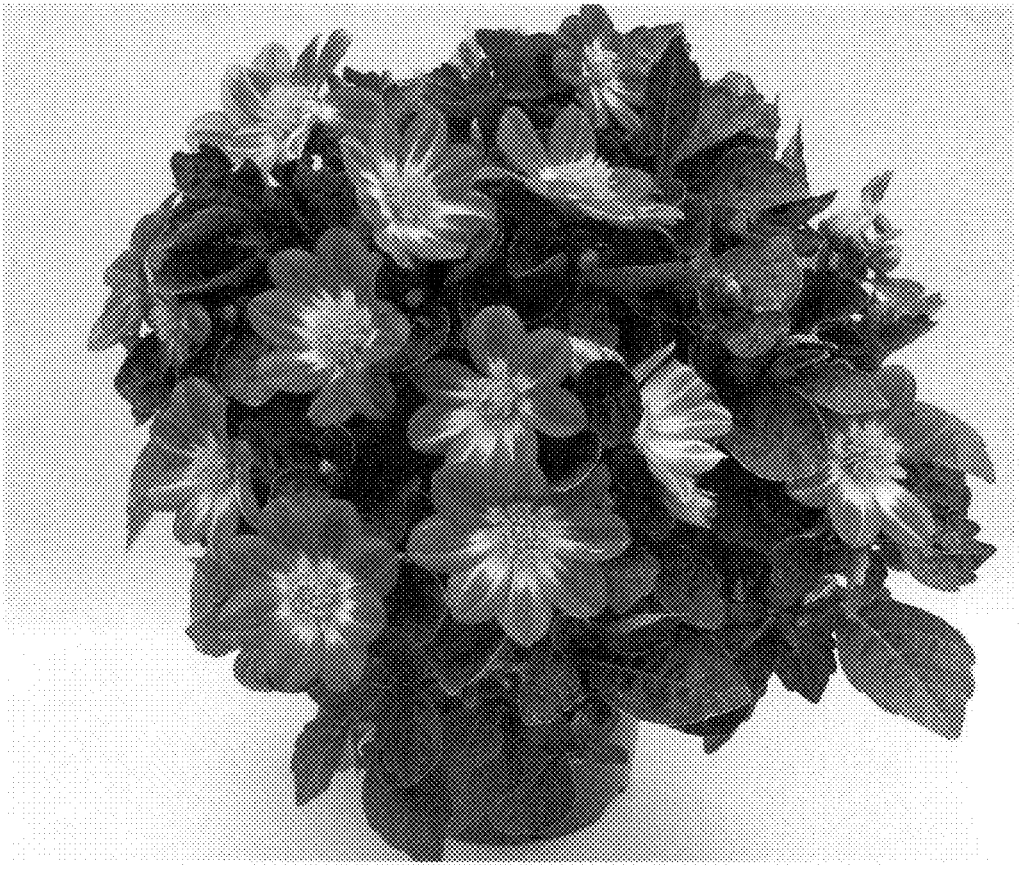
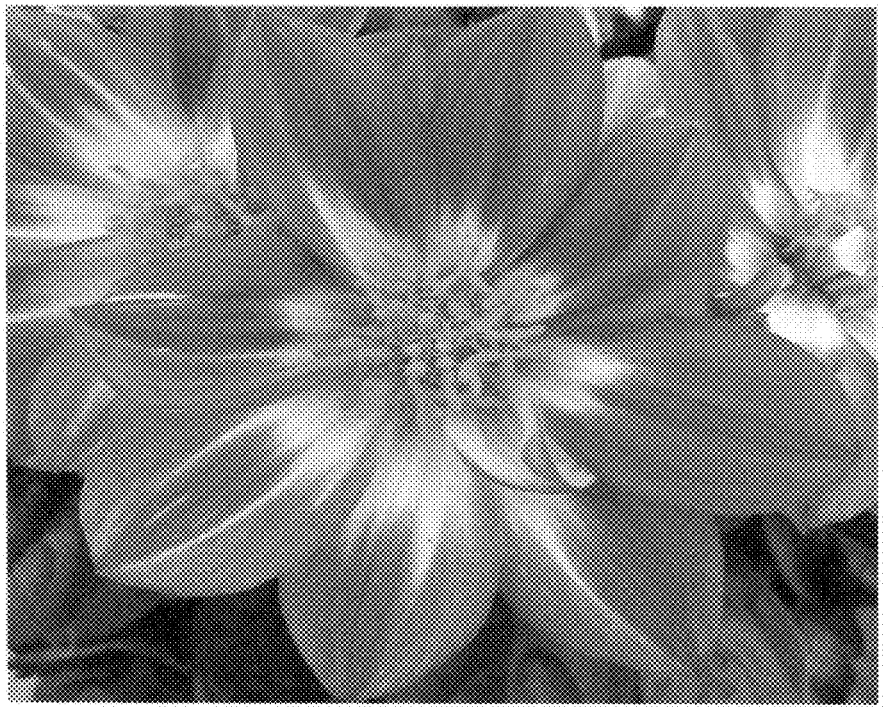

* * * * *